United States Patent

Adams

[11] 4,000,042
[45] Dec. 28, 1976

[54] DIAGNOSTIC REAGENT FOR THE DETERMINATION OF AMYLASE

[75] Inventor: Thomas H. Adams, Mission Viejo, Calif.

[73] Assignee: E. I. Du Pont de Nemours and Company, Wilmington, Del.

[22] Filed: Jan. 20, 1975

[21] Appl. No.: 542,236

Related U.S. Application Data

[63] Continuation-in-part of Ser. No. 394,823, Sept. 6, 1973, Pat. No. 3,879,263.

[30] Foreign Application Priority Data

Aug. 23, 1974 Netherlands ............ 7411234

[52] U.S. Cl. .............. 195/103.5 R; 195/99; 195/103.5 C; 195/63
[51] Int. Cl.$^2$ ............ C12K 1/00; G01N 31/14
[58] Field of Search ........ 195/103.5 R, 103.5 C, 195/63, 99

[56] References Cited

UNITED STATES PATENTS 3,778,350   12/1973   Bergmeyer ............ 195/103.5

OTHER PUBLICATIONS

Greenwaad et al., Die Starke, "Studies on Starch Degrading Enzymes — Part VIII", 20(5), 1968, pp. 139–150.
Okada et al., Agr. Biol. Chem., vol. 33, No. 6, (1969), pp. 900–906.

*Primary Examiner*—A. Louis Monacell
*Assistant Examiner*—Esther L. Massung

[57] ABSTRACT

Disclosed herein is a diagnostic agent for determining the α-amylase content of a sample comprising a first compound selected from the group consisting of maltotetraose, maltopentaose, and maltohexaose; and a second component comprising an appropriate glucose detecting reagent, such as glucose oxidase or glucose dehydrogenase.

11 Claims, 1 Drawing Figure

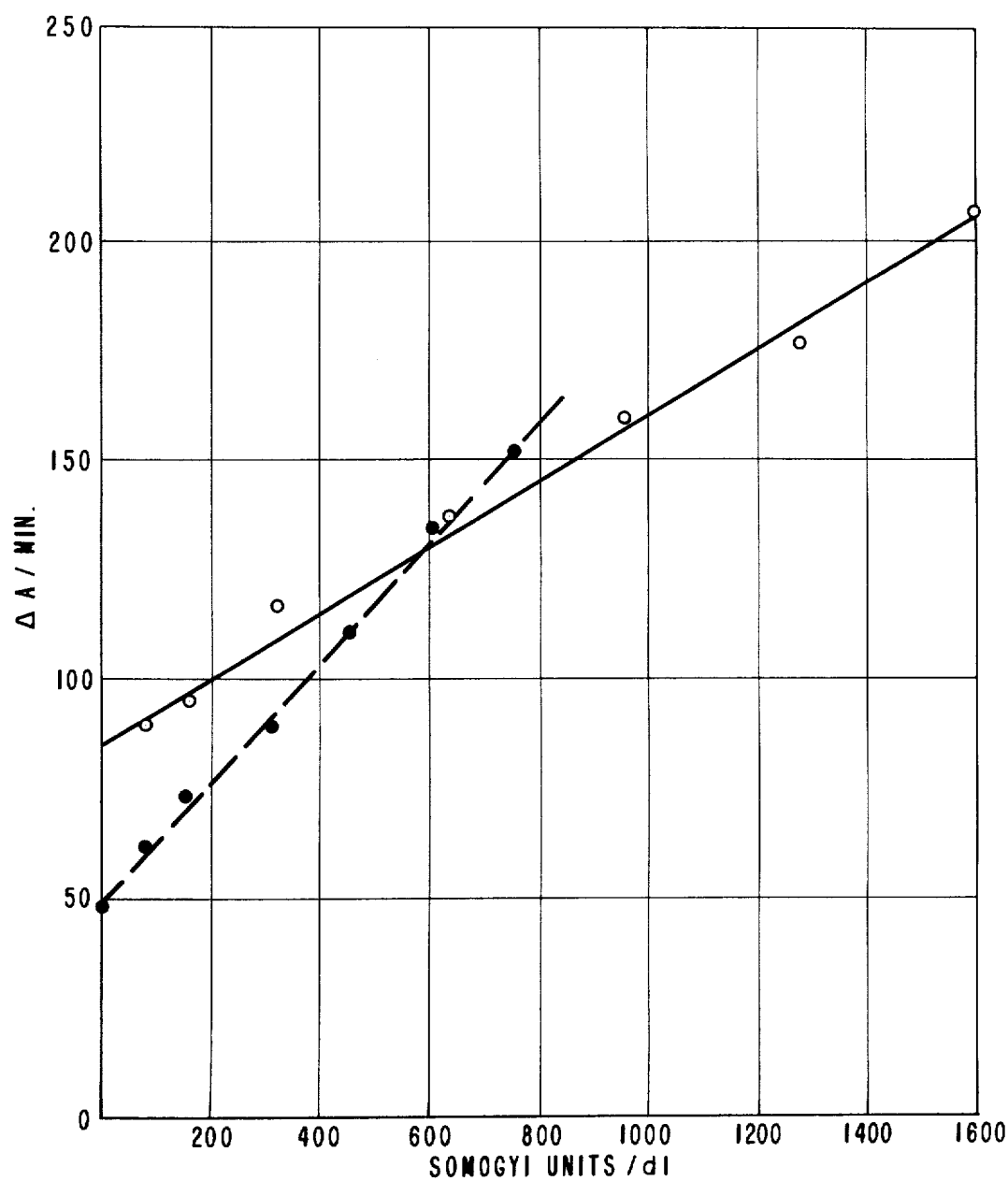

DIAGNOSTIC REAGENT FOR THE DETERMINATION OF AMYLASE

CROSS REFERENCE TO RELATED APPLICATIONS

This application is a continuation-in-part of application Ser. No. 394,823 which was filed on Sept. 6, 1973, now U.S. Pat. No. 3,879,263 by the same inventor.

BACKGROUND OF THE INVENTION

1. Field of the Invention

This invention relates to a procedure for the qualitative determination of α-amylase in a sample, and more particularly to a diagnostic agent for the enzymatic determination of α-amylase. The qualitative measurement of α-amylase concentrations in a sample is useful in medical diagnostics.

2. Discussion of the Prior Art

The enzyme α-amylase is to be found in salivary and pancreatic juices. It is well known that this enzyme reacts with various carbohydrates, particularly starch, to form maltose, and that the enzyme maltase will react with maltose to form glucose. These two reactions form the basis for intestinal digestion. See, for example, *Biochemistry* by Cantarow and Schepartz, page 263.

It is also well known that the presence of glucose can be determined by various coupled reactions. This knowledge has led to several proposed methods for measuring amylase activity in conjunction with maltose by utilizing its ability to convert starch to glucose. See, for example, the article by H. W. Schiwara in *Arztl Chab.* 17:340–343 (1971) and the paper entitled *Columetric Rate Determination of Serum Amylase Activity* given at the National Symposium on Enzyme Chemistry in 1972.

Techniques involving starch, however, do not allow truly quantitative amylase determinations. The amylase reacts with each of the constituents of starch to produce different reaction products, and the kinetics are unpredictable. This is particularly troublesome in rate determinations where the measurements are made within a short span of time, during which the reaction kinetics are even less predictable. As a result of this, measurements made using starch as the substrate for α-amylase activity do not, and in fact cannot, give a true measure of α-amylase concentrations in the test sample.

Furthermore, the test proceedings of the prior art are not capable of differentiating between salivary α-amylase and pancreatic α-amylase.

It is an object of the present invention to provide a diagnostic agent for the determination of α-amylase which allows quantitative measurements to be made. It is a further object of this invention to provide a diagnostic agent which can be used in a rate determination process for the determination of amylase so that a rapid quantitative measurement of the amount of amylase present in a sample can be made.

SUMMARY OF THE INVENTION

These and other objects are accomplished by a diagnostic agent for the determination of α-amylase comprising a first component selected from the group consisting of maltotetraose, maltopentaose, or maltohexaose; and a second component comprising an appropriate glucose detecting reagent. Preferably, the agent also comprises maltase.

The use of maltotetraose or maltopentaose as the substrate produces a truly stoichiometric determination when maltohexaose is used as the substrate, however, is believed to be slight and, therefore, tolerable.

The reaction between pancreatic α-amylase and substrate will produce maltaose, maltotriose and glucose. The glucose evolving from the reaction between the pancreatic α-amylase and the substrate can be measured by any one of a number of well known techniques which will be discussed below. Salivary α-amylase, however, does not produce glucose. The reaction between the salivary α-amylase and the substrate appears to produce only maltose. If the reaction solution contained a maltase, preferably α-glucosidase, the maltose and maltotriose produced by the reaction between the substrate and the α-amylase will be converted to glucose and the glucose can be measured by any one of a number of conventional techniques. The reaction proceeds most favorably at a temperature of between about 20° and 50° C. and at a pH of between about 5 and 10.

Since the only two sources of α-amylase are the pancreas and the salivary glands, total α-amylase can be determined by a solution containing both the substrate and the maltase; pancreatic α-amylase can be determined by a solution from which the maltase is absent, and salivary α-amylase can be determined by taking the difference between the total and the pancreatic α-amylase.

In the preferred embodiment, the substrate is maltopentaose and the step of determining the glucose evolved is accomplished by measuring the rate at which glucose is evolved. In a still more-preferred embodiment β-glycerol phosphate is used as a buffer. Any other conventional buffer which will not interfere with the ability of the α-glucosidase to convert maltose into glucose can also be used.

There are a number of ways in which glucose can be determined. Any one of these ways can be used. A particularly convenient approach is to use a coupled enzyme determination for glucose. One suitable pair of coupled enzyme reactions are defined by the following:

$$\text{Glucose} + \text{ATP} \xrightarrow[\text{Mg}^{++}]{\text{hexokinase}} \text{glucose-6-phosphate} + \text{ADP}$$

$$\text{Glucose-6-phosphate} + \text{NAD} \xrightarrow{\text{G-6-PDH}} \text{6-phosphogluconolactone} + \text{NADH};$$

where ATP is adenosine triphosphate, ADP is adenosine diphosphate, NAD is β-nicotinamide-adenine dinucleotide, NADH is the reduced form of β-nicotinamide-adenine dinucleotide, NADH is G-6-PDH is glucose-6-phosphate dehydrogenase. Since the reduced form of β-nicotinamide-adenine dinucleotide absorbs light very strongly at 340 millimicrons, while the oxidized form does not, the rate at which NADH is evolved is directly proportional to the increase in absorbance of light at 340 millimicrons at constant temperature, usually 15° C. to 50° C, and constant pH. This increase can readily be measured by those skilled in the art, using a conventional spectrophotometer. Since the rate of formation of NADH is proportional to the rate at which glucose is evolved, the increase in absorbance at 340 millimicrons can be used as a direct measure of the original concentration of α-amylase in the sample. It should also be understood that other wavelengths, e.g., 366 millimicrons, can also be used for the foregoing purpose.

Another pair of coupled enzyme reactions which can be used to determine the presence of glucose are the following:

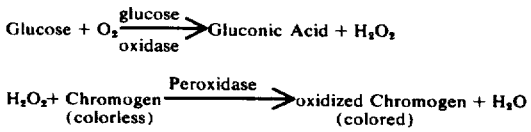

Other coupled enzyme reactions can also be used to measure the glucose content, or the glucose content may be measured directly.

Although α-glucosidase has been mentioned as the preferred maltase for use in the present invention, it should be noted that other forms of maltase can be used in the present invention. In the preferred embodiment, the substrate plus the maltase, if maltase is used, are added to the solution last. This is so that any glucose present in the sample will be used up by the other materials, prior to the introduction of the substrate. By this method, any glucose that is measured, after the substrate has been added to the solution, is due to the presence of α-amylase in the sample. The invention will be described with reference to the following examples, and FIG. 1 which is a plot of the change in absorbance ΔA per minute, in multiabsorbance units, of the reaction solution as a function of the amylase concentration in the solution for Example 1 and 2.

BRIEF DESCRIPTION OF THE FIGURE

The FIGURE shows the change in absorbance over a 5 minute period (in ΔA/minute units) for a standard solution of various amylase activity (in Somogyi Units/dl) as described in Examples 1 and 2.

EXAMPLE 1

An amylase activity standard curve was generated on a Cary 14 spectrophotometer by following the rate of change in the absorbance of NADH. The sample used for the standard curve solution was a 0.85 mg/ml solution of partially purified human pancreatic amylase dissolved in human serum. This resulted in a sample with an amylase activity of 1600 Somogyi units/dl. Dilutions of this serum were made with a 0.85% saline solution to achieve lower value.

The following solutions were used in the assay.

β-gylcerol phosphate buffer, 0.06 M, pH 6.8
NAD, 75 mg/ml $H_2O$
ATP, 30 mg/ml $H_2O$
NaCl Mg $SO_4$, 50 mg $MgSO_4$ + 30 mg NaCl/ml $H_2O$
Hexokinase, 2456 IU/ml
Glucose-6-phosphate dehydrogenase, 1000 IU/ml
maltotetraose, 200 mg/ml $H_2O$
α-glucosidase, 10 mg/ml The assay was performed as follows: To 4.50 milliliters of β-glycerol phosphate buffer, 0.1 milliliters of serum were added and allowed to equilibrate at 37° C. for 1.5 minutes. The following reagents were then added:

NAD, 0.1 ml (7.5 mg), ATP, 0.1 ml (3.0 mg)
NaCl—$MgSO_4$ − 0.05 ml (1.5 mg & 2.5 mg)
Hexokinase, 0.01 ml (25 IU)
Glucose-6-phosphate dehydrogenase, 0.01 ml (10 IU)

The reagents were mixed and the glucose in the sample was consumed in a 2 minute period. The reaction was then initiated by adding 0.04 ml α-glucosidase (10 IU) and 0.1 ml maltotetraose (20 mg). An increase in absorbance at 340 nm was monitored for 5 minutes. The change in absorbance over the 5 minute period for various solutions of the standard sample is shown by the open circles and the solid line in the figure.

EXAMPLE 2

The amylase detection system has also been adapted for automatic use by the Du Pont Automatic Clinical Analyzer (aca). Reagents for the automatic determination were prepared as described below:

1. A blend containing maltotetraose, ATP, polyethylene glycol (PEG) 2000 and β-glycerol phosphate was prepared in the following proportions: 8 mg maltotetraose; 4.8 mg ATP; 7.2 mg PEG; 5.5 mg β-glycerol phosphate and 69.4 mg mannitol. This blend was tableted producing tablets which contained 4.4 mg maltotetraose, 2.2 mg ATP.

2. A tablet was prepared containing 8.3 mg NAD, 1.9 mg $MgSO_4$, 4.1 mg PEG and 85 mg β-glycerol phosphate.

3. α-glucosidase, hexokinase and glucose-6-phosphate dehydrogenase were combined in a 50% glycerol albumin solution with 20 IU hexokinase, 18 IU glucose-6-phosphate dehydrogenase and 20 IU α-glucosidase used per test.

Analytical test packs for the aca were assembled containing two NAD, $MgSO_4$, β-glycerol phosphate buffer tablets, one maltotetraose, ATP tablet and 0.050 milliliters of the enzyme solution. These reagents were placed in the reagent compartments of a test pack such as that described in U.S. Pat. No. 3,476,515.

The aca was programmed to use 0.100 ml. of sample, 4.9 ml of water, and to report the results of the assay in milliabsorbance units/minute. The sample used was similar to that used in Example 1 except that the sample had an amylase activity of 750 Somogyi units/dl. Detection of this sample were also made as disclosed in Example 1.

The results of tests on various dilutions of the sample are represented by the solid clots and the dashed line in the figure.

EXAMPLE 3

Comparisons of the relative specificity of maltotetraose were made. Purified human pancreatic α-amylase and human salivary α-amylase were compared as to their abilities to react with the substrate maltotetraose. In the presence of the complete coupling system, α-glucosidase, ATP, NAD and G-6-PDH, both amylases appeared to react similarly. However, in the absence of the α-glucosidase, the salivary enzyme did not produce any glucose. This means that the salivary enzyme splits the maltotetraose into two maltose molecules only. The pancreatic enzyme produces a significant amount of glucose by its action on the maltotetraose directly. Thus, the method provides a means to determine the salivary and pancreatic amylase contributions to the gross rate, by running an additional assay in the absence of α-glucosidase.

EXAMPLE 4

The specificity of maltopentaose was compared with that of maltotetraose using the following reagents:

2 NAD, MgSO$_4$, β-glycerol phosphate buffer tablets (Of Example 2)
3 mg ATP
5 mg maltotetraose or 2.2 mg maltopentose
25 units hexokinase
28 units glucose-6-phosphate dehydrogenase
7 units α-glucosidase Tablets were dissolved in 4.90 ml water and the reagents listed above were added to this solution. 0.020 milliliters of the sample of Example 1 were added to this solution. A blank reagent was run in the absence of sample and the change in absorbance (ΔA) was measured at 340 nm after a 4 minute incubation in a Cary 14 spectrometer at 37° C. The results were as follows:

|       | Substrate     | ΔA/min. |
|-------|---------------|---------|
| test  | maltotetraose | .078    |
| blank |               | .026    |
| test  | maltopentaose | .101    |
| blank |               | .0015   |

The results show that the observed rate with the same sample is higher for maltopentaose than for maltotetraose. In addition, the blank rate, i.e., the reaction of the α-glucosidase with substrate is much higher with maltotetraose and is less desirable. Thus, maltopentaose would appear to be highly sensitive and would eliminate the need for closely monitoring the extent of the blank reaction.

What is claimed is:
1. Diagnostic agent for the determination of α-amylase in a body fluid comprising:
   a. a first component selected from the group of reagents consisting of maltotetraose, maltopentaose and maltohexaose; and
   b. a second component comprising an enzymatic glucose detecting reagent.
2. The agent of claim 1 wherein said second component comprises a glucose detecting reagent selected from the group consisting of glucose oxidase and glucose dehydrogenase.
3. Diagnostic agent for the determination of α-amylase in a body fluid comprising:
   a. maltotetraose; and
   b. a second component comprising an enzymatic glucose detecting reagent.
4. Diagnostic agent for the determination of α-amylase in a body fluid comprising:
   a. maltopentaose; and
   b. a second component comprising an enzymatic glucose detecting reagent.
5. Diagnostic reagents for the determination of salivary α-amylase in a body fluid comprising:
   a. a first component selected from the group of reagents consisting of maltotetraose, maltopentaose, and maltohexaose;
   b. a second component comprising maltase; and
   c. a third component comprising an enzymatic glucose detecting reagent.
6. The agent of claim 5 wherein said first component is maltotetraose.
7. The agent of claim 5 wherein said first component is maltopentaose.
8. The agent of claim 5 wherein said maltase is α-glucosidase.
9. The agent of claim 5 wherein said second component comprises a glucose detecting reagent selected from the group consisting of glucose oxidase and glucose dehydrogenase.
10. The agent of claim 1 further comprising α-glucosidase.
11. The agent of claim 5, further comprising α-glucosidase.

* * * * *